(12) United States Patent
Recanati

(10) Patent No.: US 6,736,802 B1
(45) Date of Patent: May 18, 2004

(54) EYE-DROP APPLICATOR

(76) Inventor: Shai Recanati, 250 Mercer St., New York, NY (US) 10012

( * ) Notice: Subject to any disclaimer, the term of this patent is extended or adjusted under 35 U.S.C. 154(b) by 0 days.

(21) Appl. No.: 10/308,272

(22) Filed: Dec. 4, 2002

(51) Int. Cl.[7] .......................... A61M 35/00; B65D 47/18
(52) U.S. Cl. ........................................ 604/295; 222/420
(58) Field of Search ................... 604/295–302, 604/94.01; 222/420

(56) References Cited

U.S. PATENT DOCUMENTS

| | | | | |
|---|---|---|---|---|
| 676,379 A | * | 6/1901 | Young | ................. 601/37 |
| 852,827 A | * | 5/1907 | Dorment | ................. 601/13 |
| 2,722,216 A | | 11/1955 | Robbins | |
| 2,734,665 A | * | 2/1956 | Flamm | ................ 222/207 |
| D187,170 S | | 2/1960 | Hill | |
| 4,257,417 A | | 3/1981 | Gibilisco | |
| 4,471,890 A | * | 9/1984 | Dougherty | ................ 222/190 |
| 5,261,572 A | * | 11/1993 | Strater | ................ 222/215 |
| 5,665,079 A | | 9/1997 | Stahl | |
| 5,713,495 A | | 2/1998 | Menard | |
| 5,989,217 A | * | 11/1999 | Ohki et al. | ............... 604/94.01 |
| 6,090,086 A | | 7/2000 | Bolden | |
| 6,516,795 B1 | * | 2/2003 | Bougamont et al. | ... 128/200.14 |

* cited by examiner

Primary Examiner—John J. Calvert
Assistant Examiner—Linh Truong

(57) ABSTRACT

An eye-drop applicator for directing eye-drop solution into a user's eye without the user blinking one's eye. The eye-drop applicator includes a container having a neck portion and also having an open end for storing eye-drop solution; and also includes a lid having a wall and being closable upon the open end of the container; and further includes a tubular eyedropper member being attached to the lid and through which eye-drops are dispensed from the container.

3 Claims, 3 Drawing Sheets

EYE-DROP APPLICATOR

BACKGROUND OF THE INVENTION

1. Field of the Invention

The present invention relates to eyedroppers and more particularly pertains to a new eye-drop applicator for directing eye-drop solution into a user's eye without the user blinking one's eye.

2. Description of the Prior Art

The use of eyedroppers is known in the prior art. More specifically, eyedroppers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,665,079; 4,257,417; 5,713,495; 6,090,086; 2,722,216; and Pat. No. Des. 187,170.

While these devices fulfill their respective, particular objectives and requirements, the aforementioned patents do not disclose a new eye-drop applicator. The prior art describes inventions having bottles and having eye-drop dispensers for dispensing eye-drop solution from the bottles.

SUMMARY OF THE INVENTION

The general purpose of the present invention, which will be described subsequently in greater detail, is to provide a new eye-drop applicator which has many of the advantages of the eyedroppers mentioned heretofore and many novel features that result in a new eye-drop applicator which is not anticipated, rendered obvious, suggested, or even implied by any of the prior art eyedroppers, either alone or in any combination thereof. The present invention includes a container having a neck portion and also having an open end for storing eye-drop solution; and also includes a lid having a wall and being closable upon the open end of the container; and further includes a tubular eyedropper member being attached to the lid and through which eye-drops are dispensed from the container. None of the prior art includes the combination of the elements of the present invention.

There has thus been outlined, rather broadly, the more important features of the eye-drop applicator in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new eye-drop applicator which has many of the advantages of the eyedroppers mentioned heretofore and many novel features that result in a new eye-drop applicator which is not anticipated, rendered obvious, suggested, or even implied by any of the prior art eyedroppers, either alone or in any combination thereof.

Still another object of the present invention is to provide a new eye-drop applicator for directing eye-drop solution into a user's eye without the user blinking one's eye.

Still yet another object of the present invention is to provide a new eye-drop applicator that is easy and convenient to use.

Even still another object of the present invention is to provide a new eye-drop applicator that ensures that eye-drops are dispensed into the user's eye by steadying and positioning the stem portions directly over the user's eyes.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
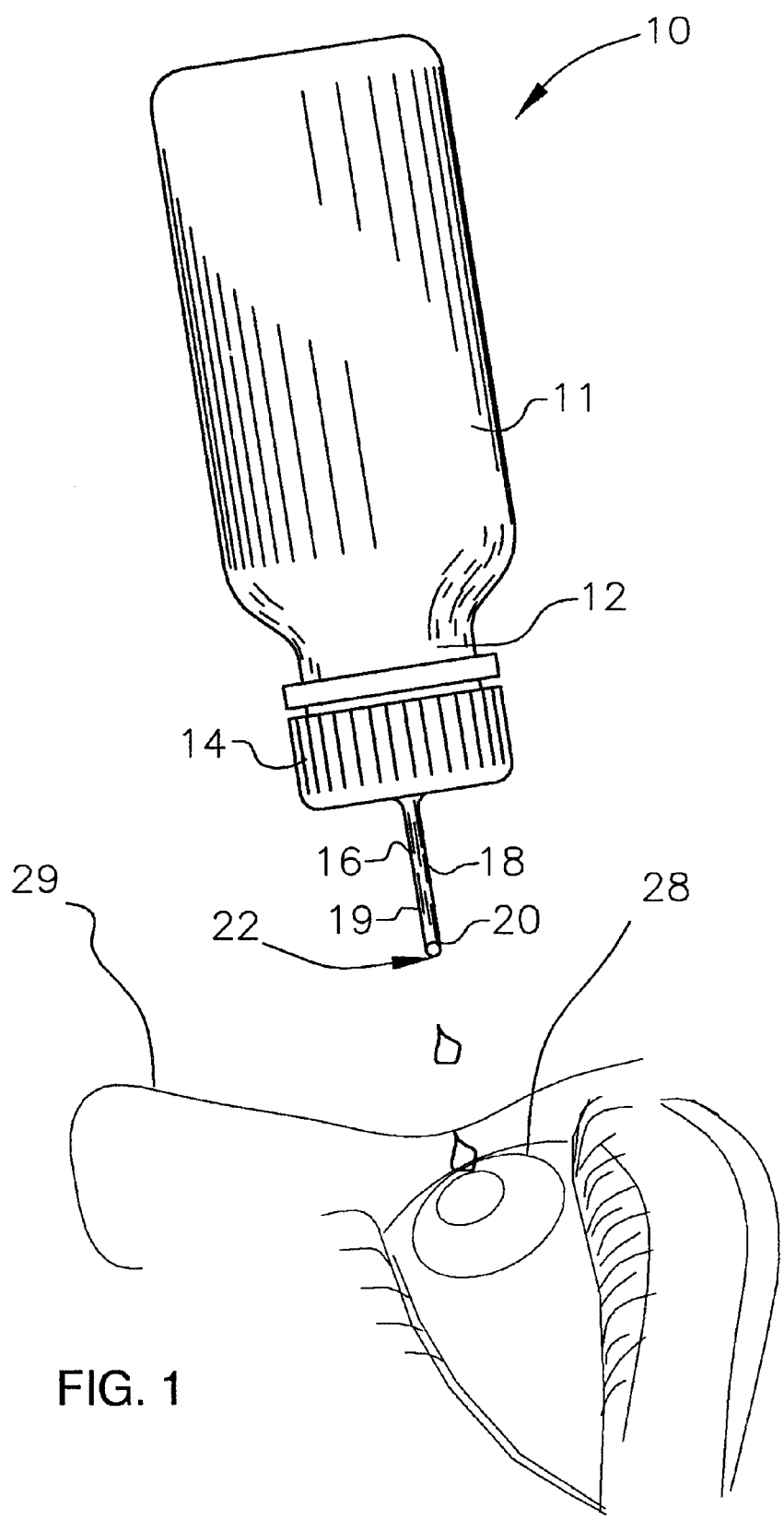
FIG. 1 is a side elevational view of a new eye-drop applicator according to the present invention.
Figure 2:
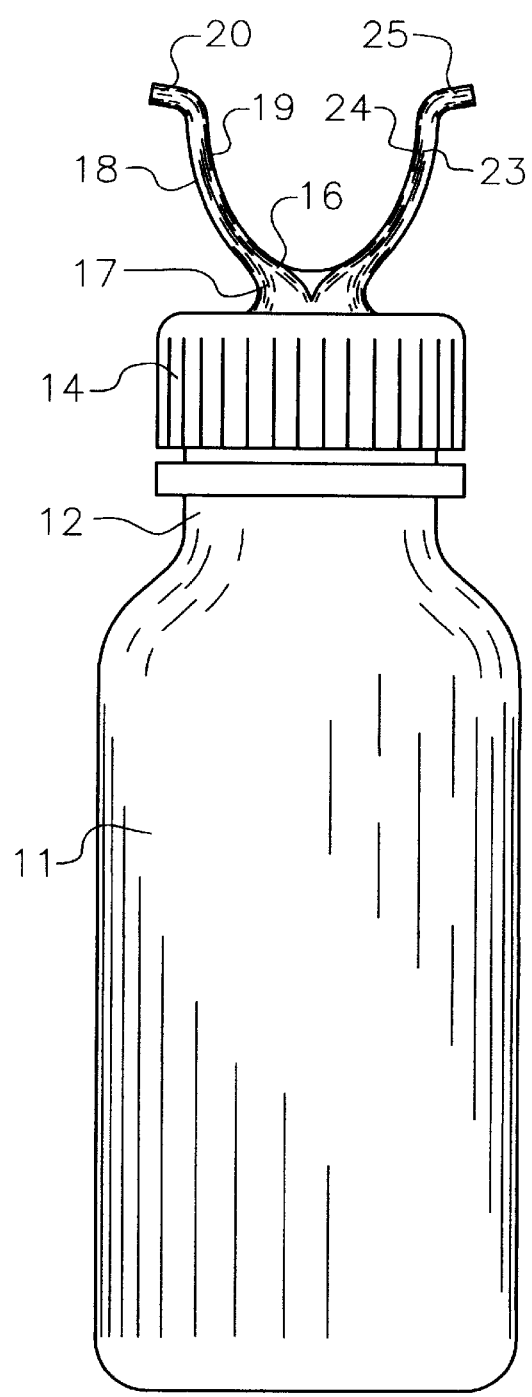
FIG. 2 is a front elevational view of the present invention.
Figure 3:
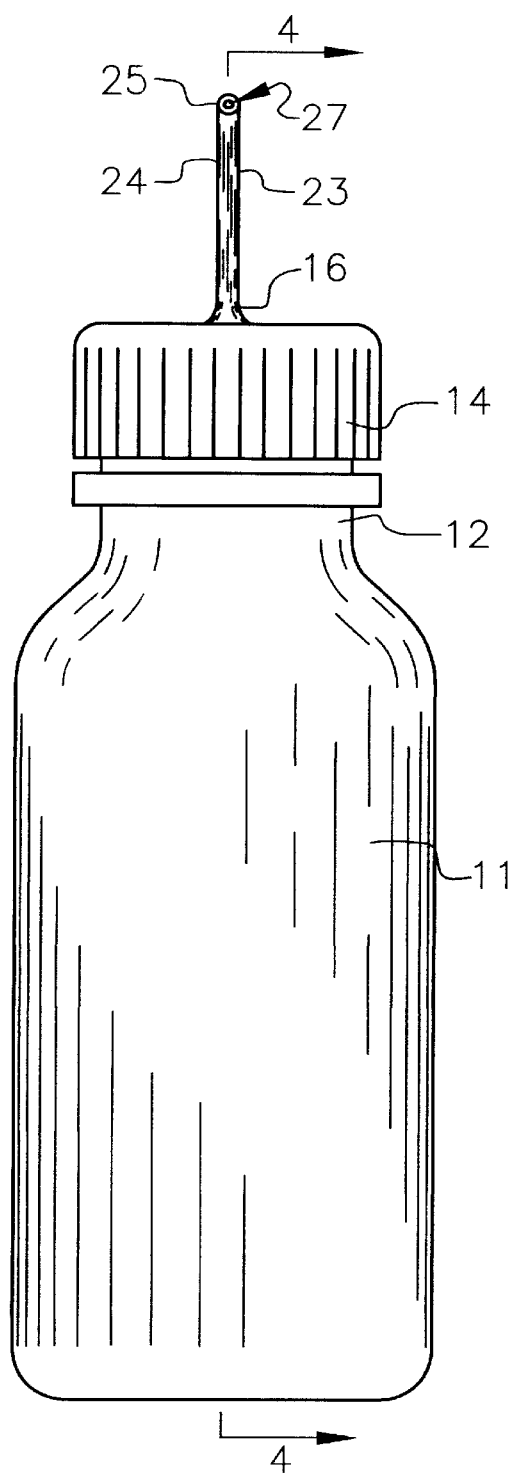
FIG. 3 is a side elevational view of the present invention.
Figure 4:
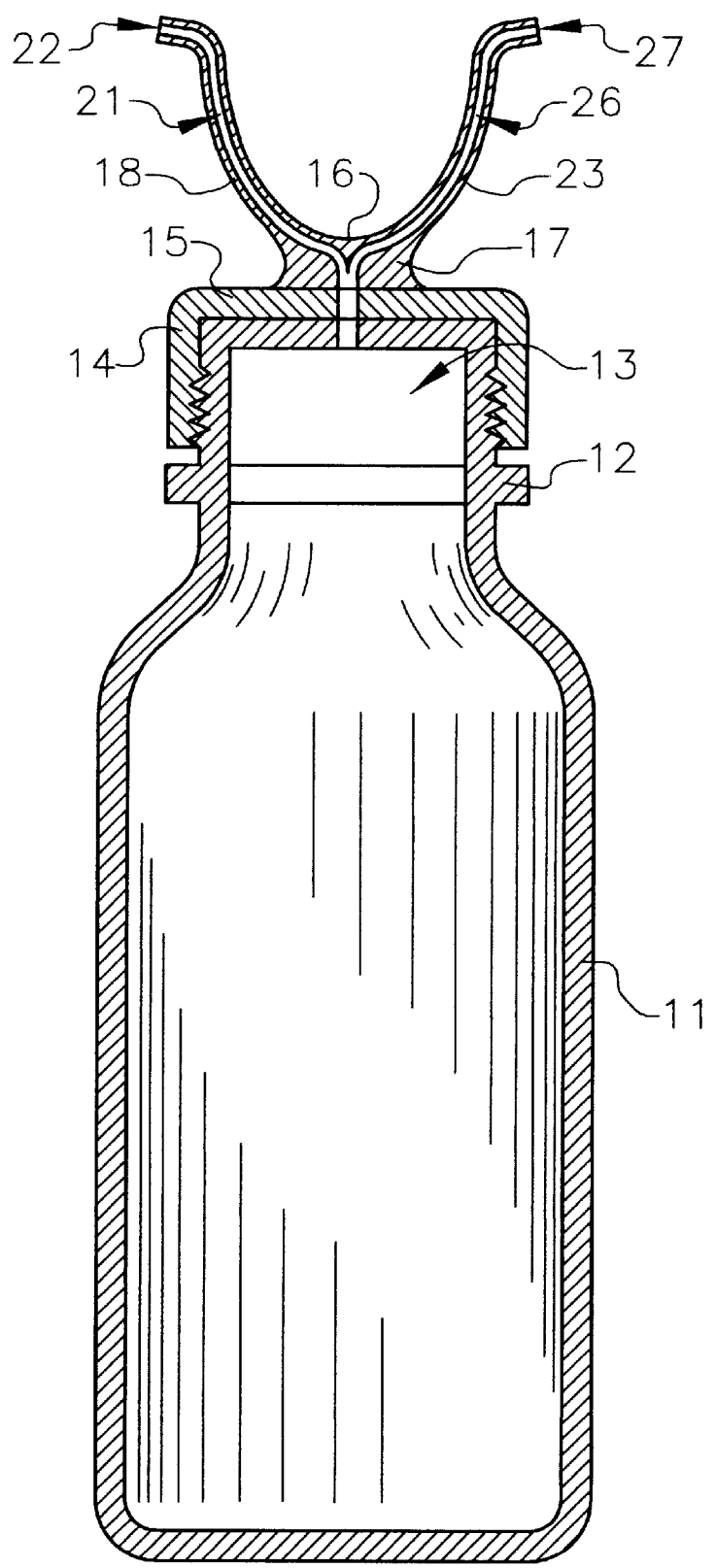
FIG. 4 is a cross-sectional view of the present invention.

With reference now to the drawings, and in particular to FIGS. 1 through 4 thereof, a new eye-drop applicator embodying the principles and concepts of the present invention and generally designated by the reference numeral 10 will be described.

As best illustrated in FIGS. 1 through 4, the eye-drop applicator 10 generally comprises a container 11 having a neck portion 12 and also having an open end 13, for storing eye-drop solution; and also comprises a lid 14 having a wall 15 and being conventionally closable upon the open end 13 of the container 11.

A tubular eyedropper member 16 is integrally attached to the lid 14 and through which eye-drops are dispensed from the container 11. The tubular eyedropper member 16 is generally U-shaped and includes a base portion 17 being integral to the wall 15 of the lid 14 and also includes a pair of stem portions 18,23 being spaced apart and extending from the base portion 17. The tubular eyedropper member 16 has passageways 21,26 extending through the base portion 17 and through the pair of stem portions 18,23. The base portion 17 of the tubular eyedropper member 16 is a bulbous mass. Each of the stem portions 18,23 has an open outer end 22,27 and also has an arcuate-shaped main portion 19,24 and an end portion 20,25 which is angled relative to the arcuate-shaped main portion 19,24. The end portions 20,25 of the pair of stem portions 18,23 extend in opposite directions from one another. The stem portions 18,23 are made of flexible plastic and are capable of being spread apart from one another and are also adapted to receive a user's nose 29 therebetween.

In use, the user places the stem portions 18,23 to either side of one's nose 29 with the user's nose 29 being used to steady the eye-drop applicator with the end portions 20,25 of the stem portions 18,23 being positioned over the user's eyes 28. The user, then, directs the container 11 such that eye-drop solution is dispensed from the container 11 and through the passageways 21,26 and through the open ends 22,27 of the stem portions 20,25 and onto the user's eyes.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the eye-drop applicator. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An eye-drop applicator comprising:

a container having a neck portion and also having an open end for storing eye-drop solution;

a lid having a wall and being closable upon said open end of said container; and a tubular eyedropper member being attached to said lid and through which eye-drops are dispensed from said container, said tubular eyedropper member being generally U-shaped and including a base portion being integral to said wall of said lid and also including a pair of stem portions being spaced apart and extending from said base portion, said tubular eyedropper member having passageways extending through said base portion and through said pair of stem portions, said base portion of said tubular eyedropper member being a bulbous mass, each of said stem portions having an open outer end and also having an arcuate-shaped main portion and an end portion which is angled relative to said arcuate-shaped main portion.

2. An eye-drop applicator as described in claim 1, wherein said end portions of said pair of stem portions extend in opposite directions from one another.

3. An eye-drop applicator as described in claim 2, wherein said stem portions are made of flexible plastic and are capable of being spread apart from one another and are also adapted to receive a user's nose therebetween.

* * * * *